United States Patent [19]

Redaelli et al.

[11] 4,226,810

[45] Oct. 7, 1980

[54] SPLITTING UP PYRAN RINGS

[75] Inventors: Vincenzo Redaelli, Mariano Comense; Renato De Simone, Como; Edoardo Platone, San Donato Milanese, all of Italy

[73] Assignee: Anic, S.p.A., Palermo, Italy

[21] Appl. No.: 964,137

[22] Filed: Nov. 28, 1978

[30] Foreign Application Priority Data

Jan. 3, 1978 [IT] Italy .................... 19008 A/78

[51] Int. Cl.$^3$ .................................. C07C 45/56
[52] U.S. Cl. .................................. 568/386; 568/414; 568/417
[58] Field of Search .................... 260/593 R, 594

[56] References Cited

U.S. PATENT DOCUMENTS

| | | | |
|---|---|---|---|
| 2,624,764 | 1/1953 | Emerson et al. | 260/593 R |
| 3,009,959 | 11/1961 | Heath et al. | 260/593 R |
| 3,255,258 | 6/1966 | Charles et al. | 260/593 R |
| 3,686,321 | 8/1972 | Mueller et al. | 260/593 R |
| 3,864,403 | 2/1975 | Ember | 260/593 R |

OTHER PUBLICATIONS

Stone et al., J. Org. Chem., vol. 42(12), pp. 2151-2154 (1977).

*Primary Examiner*—Natalie Trousof
*Assistant Examiner*—James H. Reamer
*Attorney, Agent, or Firm*—Morgan, Finnegan, Pine, Foley & Lee

[57] ABSTRACT

A chemical method for splitting the pyran ring of compounds such as 2,6,6-trimethyl-5,6-dihydro-4H-pyran is disclosed which consists in reacting the 4H-pyran derivatives concerned with water and a halogen-containing or halogen-donating catalyst at a comparatively low temperature, i.e. from 50° C. to 130° C. Interesting results are obtained and a selection field is afforded as regards the products of the pyran-ring cleavage.

8 Claims, No Drawings

SPLITTING UP PYRAN RINGS

This invention relates to a novel method for the cleavage of pyran rings. More particularly, the invention relates to a method for splitting up the ring structure of the 2,6,6-trimethyl-5,6-dihydro-4H-pyran

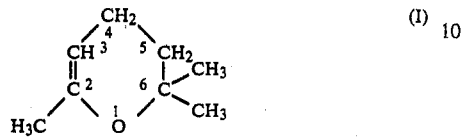

to give products (methylheptenone and/or methylheptanolone) which find a widespread use as raw materials for the synthesis of terpenes and terpene-like compounds having a great utility and diffusion.

Reference will be had, when describing the method according to this invention, to the cleavage of the above cited compound, which, by virtue of the products which can derive from it, is the most interesting from the point of view of the subsequent applications. Be it understood, at any rate, that what will be said hereinafter applies equally well to pyrans which carry different substituents and it will be easy for anyone skilled in the art, once the basic principle of the invention has been appraised, to adapt it to other substrates without departing from the scope of the invention.

Thus, starting from the compound (1), the subject matter of the present invention is to provide a method for cleaving its ring structure, said method comprising the step of heating such compound in the presence of water and of small amounts of an appropriate catalytic system.

The importance of methylheptenone as an intermediate for the synthesis of a number of terpene compounds (linalol, citral, ionones, vitamin A and others), which find uses in the food, pharmaceutical and perfuming substances fields, just to cite the most common ones, is known long since.

Now, one of the most common and most frequently adopted methods for the synthesis of methylheptenone starts from isobutene, formaldehyde and acetone, or from isobutene and methylvinylketone (separately prepared from formaldehyde and acetone), working at 200° C.–300° C. and under a pressure of a few hundreds of atmospheres, and obtains as an intermediate which is the pyran compound (I).

Conversely, it was difficult to split up the pyran ring directly. For example, the German Pat. No. 1 259 876 provided for such a step but at 290° C.–300° C. under a pressure of 80 to 90 atm, in the presence of 0.1% to 3% of water on a weight basis.

As outlined above, the present Applicants have found that it is possible to split up the pyran compound (I) under particularly bland conditions.

The reaction according to the invention is performed by merely heating the compound (I), in the presence of water and of a catalyst composed by a compound (or an admixture of compounds) which is capable of setting free halogens under the reaction conditions.

The resultant product, which is a function of the quantity of catalyst which has been used, can predominantly consist of methylheptenone, in the form of a mixture of the two isomers thereof.

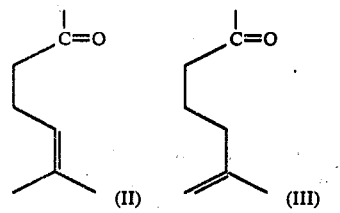

or it may consist of methylheptanolone (6-hydroxy-6-methyl-heptane-2-one):

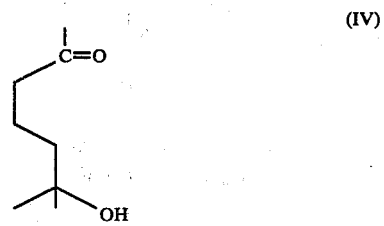

Thus, for example, a quantity of catalyst of from 0.1% to 1% based on the weight of (I) can give rise to the two isomers cited above, whereas lower levels of catalyst encourage the formation of methylheptanolone (IV).

More detailedly, the reaction outlined above takes place in the presence of an amount of water which can be varied from 0.2 to 2 mols of water per mol of (I) and an amount of catalyst which can be varied from 0.01% to 1% by weight based on the weight of (I) consistently with the product (or admixture of products) one desires to obtain, the reaction mixture being heated beforehand to a temperature in the range from 50° C. to 130° C. The catalyst to be used is selected from among the halogens, the interhalogen compounds or the compounds which are capable of setting free halogens under the reaction conditions. It should be added, lastly, that the reaction can take place both with a solvent medium being present and without solvents. In the former case, the solvent can be selected from among the hydrocarbons or from compounds which solubilize also water.

All the working details will become anyhow clearer from the scrutiny of the ensuing illustrative examples which, however, are not to be construed as limitations to the invention.

EXAMPLE 1

A 2-ml thick-walled glass tube (Supelco Inc.) is charged with 0.85 g of 2,6,6-trimethyl-5,6-dihydro-4H-pyran (I) having a 98% purity (gaschromatographically) together with 0.12 g of water and 0.0009 g of iodine ($H_2O$/pyran=1/1 mol approx.)

After having evacuated the tube through the rubber stopper seal the tube is immersed in an oil bath thermostatically controlled at 100° C. After 3 hrs the contents of the tube is analyzed gaschromatographically, taking o-xylene as the internal standard.

It is found that the pyran has been converted for 90% with a molar selectivity of 80% of methylheptenone (mixture of alpha and beta isomers in a ratio of 85/15 approx.) and of 15% of methylheptanolone (IV).

Since it is possible, as is known, to convert nearly quantitatively methylheptanolone to pyran (which can be recycled to the pyran→methylheptenone reaction), or to methylheptenone, it can be said that under the conditions of the present example about 95% of the pyran which has been reacted is conducive to methylheptenone.

EXAMPLE 2

Operating under the same conditions of Example 1, the tube is charged, together with 0.88 g of pyran (I) and 0.13 g of water, with 0.0020 g of bromine.

After 2 hrs at 100° C., the conversion of the pyran is 73%, with a 87% (molar) of selectivity of methylheptenone (mixture beta/alpha approximately 85/15). After 4 hrs the conversion is about 80% and the selectivity, intended as above, is 90%.

EXAMPLE 3

Operating under the same conditions of Example 1, there are charged 1 ml of dioxan, 0.43 g of pyran (I), 0.06 g of water and 0.0023 g of iodine. After one hour at 100° C., the conversion of the pyran is 91%, the molar selectivity of methylheptenone (mixture beta/alpha=85/15 approximately) is 68% and the selectivity of methylheptanolone is 16%.

EXAMPLE 4

Operating with the same procedure as in Example 3, there are charged: 1 ml of dioxan, 0.43 g of pyran, 0.06 g of water and 0.0016 g of $I_2$. After one hour at 100° C. a 83.0% conversion is found with a selectivity of methylheptenone of 51.3% and a selectivity of methylheptanolone of 32%.

EXAMPLE 5

Operating as in the previous Example, but carrying out the reaction at 130° C., after one hour there are found: conversion 97.2%, molar selectivity of methylheptenone 61.5% and molar selectivity of methylheptanolone 8.5%.

EXAMPLE 6

Operating as in the previous Example but at 120° C., after one hour the following is obtained: conversion 95.5%, molar selectivity of methylheptenone 71.2% and molar selectivity of methylheptanolone 6.6%.

EXAMPLE 7

Operating as in the previous Example but at 80° C. there is obtained after one hour: conversion of 80.5%, molar selectivity of methylheptenone 20.1% and molar selectivity of methylheptanolone 61.4%.

EXAMPLE 8

Operating as in the previous Example but at 60° C. after one hour the following is obtained: conversion of 65.6%, molar selectivity of methylheptenone 6.6% and molar selectivity of methylheptanolone 67.5%.

EXAMPLE 9

Operating as described in Example 1, but charging 1 ml of dioxan, 0.03 g of water, 0.43 g of pyran (I), 0.00138 g of iodine in the form of 60 mls of a 0.092 M solution of $I_2$ in dioxan. After one hour at 100° C., there have been calculated a conversion of 88.1%, a molar selectivity of methylheptenone (alpha+beta) of 57.0% and a molar selectivity of methylheptanolone of 15.6%, respectively.

EXAMPLE 10

Operating as in the previous Example, but reducing the water amount to 0.01 g, the analysis of the mixture, after one hour at 100° C., gives the following results: conversion 60.0%, molar selectivity of methylheptenone 40.3% and molar selectivity of methylheptanolone 13.3%.

EXAMPLE 11

Also in this case the procedure is quite similar to that of Example 1, by charging 0.5 ml of dioxan. 0.47 g of pyran (I), 0.08 g of water and 0.00023 g of iodine, in the form of 10ml of a 0.092 M solution in dioxan ($I_2$ is about 0.05% by wt relative to the pyran). After one hour at 100° C., the conversion of the pyran (I) is 96%, its molar selectivity in methylheptenone (alpha+beta) is 5% and the molar selectivity in methylheptanolone is 95%.

EXAMPLE 12

By following the same procedure as in the previous Example but charging 1 ml of dioxan, 0.06 g of water, 0.43 g of pyran (I) and 0.00011 g of iodine, in the form of 5 mls of a 0.092 M solution of $I_2$ in dioxan, there are obtained, after one hour at 100° C., the following results: conversion 72.5%, molar selectivity of methylheptenone (alpha+beta) 1.3% and molor selectivity of methylheptanolone 92.2%.

We claim:
1. A process for splitting up the ring 2,6,6-trimethyl-5,6-dihydro-4H-pyran comprising the step of heating same in the presence of a water and a halogen catalyst.
2. A process according to claim 1, characterized in that heating is carried out at a temperature comprised between 50° C. and 130° C.
3. A process according to claim 1, characterized in that the reaction takes place in the presence of an amount of water variable between 0.2 mol and 2 mols per mol of pyran.
4. A process according to claim 1, characterized in that the reaction takes place in the presence of an amount of catalyst variable from 0.01% to 1% by wt relative to the weight of pyran.
5. A process according to claim 4 wherein said catalyst is iodine.
6. A process according to claim 4 wherein said catalyst is bromine.
7. A process according to claim 2 wherein said catalyst is iodine.
8. A process according to claim 2 wherein said catalyst is bromine.

* * * * *